United States Patent
Murano et al.

(10) Patent No.: US 10,435,360 B2
(45) Date of Patent: Oct. 8, 2019

(54) METHOD OF PURIFYING DIMETHYL SULFOXIDE

(71) Applicant: Toray Fine Chemicals Co., Ltd., Tokyo (JP)

(72) Inventors: Haruo Murano, Ichihara (JP); Katsuhiro Shibayama, Ichihara (JP)

(73) Assignee: Toray Fine Chemicals Co., Ltd., Tokyo (JP)

(*) Notice: Subject to any disclaimer, the term of this patent is extended or adjusted under 35 U.S.C. 154(b) by 0 days.

(21) Appl. No.: 15/781,874

(22) PCT Filed: Nov. 21, 2016

(86) PCT No.: PCT/JP2016/084414
§ 371 (c)(1),
(2) Date: Jun. 6, 2018

(87) PCT Pub. No.: WO2017/098900
PCT Pub. Date: Jun. 15, 2017

(65) Prior Publication Data
US 2018/0354899 A1    Dec. 13, 2018

(30) Foreign Application Priority Data
Dec. 9, 2015 (JP) ................. 2015-240081

(51) Int. Cl.
*C07C 315/06* (2006.01)
*C07C 317/04* (2006.01)

(52) U.S. Cl.
CPC .......... *C07C 315/06* (2013.01); *C07C 317/04* (2013.01)

(58) Field of Classification Search
CPC .................................................. C07C 315/06
See application file for complete search history.

(56) References Cited

U.S. PATENT DOCUMENTS

2009/0005601 A1*  1/2009  Kvakovszky ......... C07C 315/06
568/27

FOREIGN PATENT DOCUMENTS

| JP | 38-20721 | 10/1963 |
| JP | 43-3765 | 2/1968 |
| JP | 2015-145359 A | 8/2015 |

OTHER PUBLICATIONS

Thomas M. Santosusso et al., "Chemistry of epoxides. XXXII. Acid catalysis in dimethyl sulfoxide reactions. A generally unrecognized factor," The Journal of Organic Chemistry, vol. 41, No. 16, Aug. 1976, pp. 2762-2768 (Abstract).

* cited by examiner

*Primary Examiner* — Rosalynd A Keys
(74) *Attorney, Agent, or Firm* — DLA Piper LLP (US)

(57) ABSTRACT

A method of purifying dimethyl sulfoxide includes distilling a dimethyl sulfoxide-containing liquid in the presence of sodium carbonate in an inert gas atmosphere to distill out dimethyl sulfoxide, an amount of the sodium carbonate with respect to 100 g of pure dimethyl sulfoxide in a residual liquid after the distillation being 6 times or more the amount of the sodium carbonate with respect to 100 g of the pure dimethyl sulfoxide in the dimethyl sulfoxide-containing liquid before the distillation.

19 Claims, No Drawings

METHOD OF PURIFYING DIMETHYL SULFOXIDE

TECHNICAL FIELD

This disclosure relates to a method of purifying dimethyl sulfoxide (DMSO).

BACKGROUND

Dimethyl sulfoxide is widely used in industries as a solvent for polymerization of polymers and spinning polymer fibers. Additionally, recovery and reuse of dimethyl sulfoxide used once are widely performed in industry, and require steps of heating and distilling to purify.

It is, however, known that dimethyl sulfoxide is relatively thermally unstable and slightly decomposed when distilled under atmospheric pressure. In manufacturing or recovering dimethyl sulfoxide by distillation, contaminating a partially decomposed decomposition product in dimethyl sulfoxide reduces efficiency of dimethyl sulfoxide as a solvent. Thus, distillation of dimethyl sulfoxide is often performed under reduced pressure at 100° C. or less.

If dimethyl sulfoxide can be distilled, for example, at a high temperature of 110° C. or more, it is unnecessary to use high vacuum in distillation and, furthermore, no load is applied to a decompression device. Thus, facility for distillation can be simplified, which is industrially preferable.

There are known methods of adding a metal hydroxide such as sodium hydroxide or potassium hydroxide as an inhibitor for dimethyl sulfoxide decomposition (see JP-B-S43-3765, JP-B-S38-20721 and JP-A-2015-145359). The amount of addition of sodium hydroxide, potassium hydroxide or the like is limited to 0.003 to 0.5%, and adding in an amount of 1% or more promotes dimethyl sulfoxide decomposition.

In JP '765, the amount of a decomposition product quantified as formaldehyde after heating at 150° C. for 10 hours was 0.032% when no metal hydroxide was added, 0.054% when 1% of potassium hydroxide was added, and 0.052% when 1% of sodium hydroxide was added.

When purifying by distilling dimethyl sulfoxide, the purified dimethyl sulfoxide is distilled out of the system by the distillation. In addition, water contained in a dimethyl sulfoxide-containing liquid, a solvent having a lower boiling point than dimethyl sulfoxide, unreacted monomers in polymerization, and impurities such as a decomposition product of dimethyl sulfoxide are distilled out of the system by distillation. As a result, when a metal hydroxide such as sodium hydroxide or potassium hydroxide as an inhibitor for dimethyl sulfoxide decomposition is added, the metal hydroxide such as sodium hydroxide or potassium hydroxide remains at a bottom of a distillation column during purification as the distillation and purification of dimethyl sulfoxide proceed. This increases concentration of the metal hydroxide contained in a residual liquid after the distillation. In distilling dimethyl sulfoxide, even if a metal hydroxide is added at low concentration, dimethyl sulfoxide decomposition is rather promoted when dimethyl sulfoxide is distilled out and the concentration of the metal hydroxide reaches 1% or more. Thus, there has been a problem in that purity is reduced due to contaminating a decomposition product of dimethyl sulfoxide in distilled dimethyl sulfoxide.

There has been a desire for a dimethyl sulfoxide-purifying method that enables high purity dimethyl sulfoxide to be obtained safely, for example, at a high temperature of 110° C. or more and even when a decomposition inhibitor is highly concentrated in distilling and purifying dimethyl sulfoxide.

It could therefore be helpful to provide a method of purifying dimethyl sulfoxide to obtain high purity dimethyl sulfoxide.

SUMMARY

We provide a method of purifying dimethyl sulfoxide including distilling a dimethyl sulfoxide-containing liquid in the presence of sodium carbonate in an inert gas atmosphere to distill out dimethyl sulfoxide, in which an amount of the sodium carbonate with respect to 100 g of pure dimethyl sulfoxide in a residual liquid after the distillation is 6 times or more the amount of the sodium carbonate with respect to 100 g of pure dimethyl sulfoxide in the dimethyl sulfoxide-containing liquid before the distillation.

The method of purifying dimethyl sulfoxide inhibits decomposition of dimethyl sulfoxide even when the concentration of sodium carbonate increases from low to high so that high purity dimethyl sulfoxide can be obtained by distillation.

The amount of dimethyl sulfoxide decomposition is small not only in a distillate after the distillation (a main distillate and an early distillate) but also in a residual liquid after the distillation. Dimethyl sulfoxide decomposition is small in the residual liquid after the distillation or even in a liquid during the distillation so that high purity dimethyl sulfoxide can be obtained by the distillation.

The amount of dimethyl sulfoxide decomposition is small, which is calculated from dimethyl sulfoxide purity in a mixed liquid of the distillate (the main distillate and the early distillate) after distillation and the residual liquid after distillation. Thus, the sodium carbonate used in the dimethyl sulfoxide-purifying method effectively inhibits dimethyl sulfoxide decomposition.

The method of purifying dimethyl sulfoxide enables distillation to be performed at high temperature so that the method does not require any high vacuum facility and enables purification at low cost. Since sodium carbonate is safe, operation can be performed safer as compared to conventional purification methods using dangerous substances.

Dimethyl sulfoxide obtained by the method of purifying dimethyl sulfoxide can be used as solvents in steps of polymerizing and spinning polymers such as polyacrylonitrile, cellulose, polyimide, polysulfone, and polyurethane, stripping liquids for photoresists that are electronic materials, solvents used in synthesizing pharmaceuticals and agrochemicals, removing and cleaning liquids for lens molds and the like, or liquids used in paint stripping.

DETAILED DESCRIPTION

We provide a method of purifying dimethyl sulfoxide, including distilling a dimethyl sulfoxide-containing liquid in the presence of sodium carbonate in an inert gas atmosphere to distill out dimethyl sulfoxide, in which an amount of the sodium carbonate with respect to 100 g of pure dimethyl sulfoxide in a residual liquid after the distillation is 6 times or more the amount of the sodium carbonate with respect to 100 g of the pure dimethyl sulfoxide in the dimethyl sulfoxide-containing liquid before the distillation.

The sodium carbonate may be either an anhydride or hydrate, and the hydrate is preferably a monohydrate or decahydrate that are easily available.

The sodium carbonate may be added in powder or solid form as it is or may be added as an aqueous solution. When added as an aqueous solution, the sodium carbonate can be automatically and continuously charged at a uniform concentration in a distillation apparatus, which is therefore preferable in terms of safety. The concentration of the sodium carbonate when prepared into an aqueous solution can be increased up to a concentration saturated at a temperature used. When adding a sodium carbonate as an aqueous solution, the amount of the sodium carbonate to be added is preferably 0.1 to 35 g, more preferably 0.2 to 30 g, still more preferably 1 to 30 g, and most preferably 10 to 25 g, with respect to 100 g of water.

Solubility of sodium carbonate into 100 g of water is 22 g at 20° C., which is high. Accordingly, when sodium carbonate concentration is increased by distillation and sodium carbonate crystals are deposited, the crystals in the column can be easily removed even in removing by cleaning with water due to its high water solubility.

The dimethyl sulfoxide-containing liquid may be an impurity-free and 100% dimethyl sulfoxide liquid. Additionally, the dimethyl sulfoxide-containing liquid may be a liquid containing a very small or small amount of impurity (impurities). Furthermore, the dimethyl sulfoxide-containing liquid may contain a large amount of a liquid other than dimethyl sulfoxide.

Since it is costly to distill and remove an impurity (impurities), the dimethyl sulfoxide-containing liquid before distillation preferably contains pure dimethyl sulfoxide in an amount of 10% by weight or more. The pure dimethyl sulfoxide refers to dimethyl sulfoxide with a purity of 100%. The dimethyl sulfoxide-containing liquid before distillation contains the pure dimethyl sulfoxide in an amount of more preferably 20% by weight or more, and still more preferably contains the pure dimethyl sulfoxide in an amount of from 30 to 100% by weight.

The dimethyl sulfoxide-containing liquid before distillation may contain water other than dimethyl sulfoxide. The amount of the water in the dimethyl sulfoxide-containing liquid before distillation is preferably 0.01 to 900 g, more preferably 0.1 to 400 g, still more preferably 1 to 250 g, and still further more preferably 5 to 100 g, with respect to 100 g of the pure dimethyl sulfoxide in the liquid.

When the dimethyl sulfoxide-containing liquid contains an impurity and/or the like that hinder(s) distillation such as a resin component, an insoluble substance, a component that tends to be gelled when concentrated, an acid or a strong alkali, and/or a component that reacts with dimethyl sulfoxide, it is preferable to remove, separate, inactivate, or neutralize the impurity and/or the like by previously performing filtering, adsorption and separation, addition of an activated carbon, an ion-exchange resin or a base or the like.

When distilling and purifying by adding a decomposition inhibitor in the dimethyl sulfoxide-containing liquid, purified dimethyl sulfoxide is distilled out of the system by the distillation. Additionally, water contained in the dimethyl sulfoxide-containing liquid, a solvent having a lower boiling point than dimethyl sulfoxide, unreacted monomers in polymerization, and impurities such as a decomposition product of dimethyl sulfoxide are distilled out of the system by the distillation. As a result, as distillation and purification of dimethyl sulfoxide proceed, the decomposition inhibitor remains at the bottom of the distillation column during the purification, increasing the concentration of the decomposition inhibitor in a residual liquid during the distillation. When sodium hydroxide or potassium carbonate is used as the decomposition inhibitor, even if added at low concentration, dimethyl sulfoxide decomposition is promoted when dimethyl sulfoxide is distilled out and the concentration of the decomposition inhibitor increases. Then, a decomposition product of dimethyl sulfoxide is contaminated in distilled dimethyl sulfoxide, thereby reducing dimethyl sulfoxide purity.

On the other hand, sodium carbonate inhibits decomposition of dimethyl sulfoxide even when highly concentrated by distilling-out of dimethyl sulfoxide so that high purity dimethyl sulfoxide can be obtained.

The amount of the sodium carbonate added at a start of distillation is preferably 0.0005 to 1.0 g, and more preferably 0.001 to 0.5 g with respect to 100 g of the pure dimethyl sulfoxide in the liquid.

The amount of the sodium carbonate with respect to 100 g of the pure dimethyl sulfoxide in the residual liquid after the distillation is 6 times or more the amount of the sodium carbonate with respect to 100 g of the pure dimethyl sulfoxide in the dimethyl sulfoxide-containing liquid before the distillation.

The phrase "the residual liquid after the distillation" refers to a dimethyl sulfoxide-containing liquid left at the bottom of a distillation column or in a flask at the end of distillation without being distilled when distilling the dimethyl sulfoxide-containing liquid in a distillation facility.

As long as stirring is possible, the concentration of the sodium carbonate in a residual liquid after distillation can be increased.

When the amount of the sodium carbonate with respect to 100 g of the pure dimethyl sulfoxide in the residual liquid after the distillation is below 6 times the amount of the sodium carbonate with respect to 100 g of the pure dimethyl sulfoxide in the dimethyl sulfoxide-containing liquid before the distillation, dimethyl sulfoxide recovery rate is low, thus increasing cost for purifying dimethyl sulfoxide.

The amount of the sodium carbonate with respect to 100 g of the pure dimethyl sulfoxide in the residual liquid after the distillation is preferably 6 to 1000 times, more preferably 10 to 500 times, and still more preferably 20 to 200 times as much as the amount of the sodium carbonate with respect to 100 g of the pure dimethyl sulfoxide in the dimethyl sulfoxide-containing liquid before the distillation.

The amount of the sodium carbonate after the distillation is preferably concentrated to 0.01 to 100 g, and more preferably to 0.1 to 85 g, with respect to 100 g of the pure dimethyl sulfoxide in the residual liquid after the distillation. When the amount of the sodium carbonate after the distillation is 100 g or more, slurry of the residual liquid may be hardened at the bottom of the distillation column, which may cause difficulty in stirring.

Regarding timing of sodium carbonate addition in the dimethyl sulfoxide-containing liquid, the sodium carbonate may be added before the distillation or may be added after distilling away an impurity (impurities) having a lower boiling point than dimethyl sulfoxide to perform the distillation. Additionally, sodium carbonate deposited after the distillation may be discarded or recovered and reused.

Dimethyl sulfoxide is distilled in an inert gas atmosphere. The term "inert gas atmosphere" means a nitrogen, carbon dioxide, helium, or argon atmosphere, and may be composed of one kind of gas or a mixed gas composed of two or more gases. The inert gas atmosphere is preferably a nitrogen atmosphere. When distilled in air, dimethyl sulfoxide is easily decomposed.

Dimethyl sulfoxide is distilled more preferably in an inert gas atmosphere and under atmospheric to reduced pressure. When there is a small difference in boiling point between an impurity to be desirably removed and dimethyl sulfoxide, the degree of pressure reduction is not very lowered to increase the difference in boiling point between the impurity and dimethyl sulfoxide, thereby facilitating removal of the impurity.

When distilling under atmospheric pressure, temperature during the distillation is preferably 160° C. to 200° C., more preferably 170° C. to 195° C., still more preferably 180° C. to 194° C., and still further more preferably 189° C. to 193° C., whereby no load is applied to the apparatus, and also the facility for distillation is simplified, which is industrially preferable.

When distilling under reduced pressure, distillation is performed preferably at 10 to 750 Torr, and more preferably 15 to 730 Torr.

When distilling under reduced pressure, temperature during the distillation is preferably 108° C. to 180° C., more preferably 120° C. to 170° C., and still more preferably 131° C. to 160° C.

The purity of dimethyl sulfoxide is measured by gas chromatography with a capillary column.

The purity of dimethyl sulfoxide purified is analyzed by the gas chromatography using a capillary column and represented by area %. The purity thereof is preferably 99.990% or more, more preferably 99.991% or more, and still more preferably 99.992% or more.

The amount of decomposition (area %) of dimethyl sulfoxide will be defined as below. The dimethyl sulfoxide-containing liquid before distillation is defined as "charged liquid." A liquid obtained by mixing a distillate after distillation (including a main distillate and, if any, an early distillate) and a residual liquid after the distillation is defined as "post-distillation mixed liquid." The purity (area %) of dimethyl sulfoxide in each of the charged liquid and the "post-distillation mixed liquid" was measured by the gas chromatography, and the amount of decomposition of dimethyl sulfoxide was obtained by the following calculation equation:

Amount of decomposition of dimethyl sulfoxide (area %)=purity in charged liquid (area %)−purity in post-distillation mixed liquid (area %).

The amount of decomposition of dimethyl sulfoxide is preferably 0.009 area % or less, more preferably 0.008 area % or less, and still more preferably 0.007 area % or less.

In the method of purifying dimethyl sulfoxide, distillation is applicable to both of batch distillation and continuous distillation, and the distillation column may be a single column, a composite column, or a combination of two or more distillation columns. When performing a continuous distillation, a sodium carbonate aqueous solution is preferably continuously supplied before the distillation column(s).

As for the number of theoretical plates of the distillation column(s), preferred is/are distillation column(s) with 1 to 50 theoretical plates, and suitably, more preferred is/are distillation column(s) with 3 to 40 theoretical plates.

The dimethyl sulfoxide-containing liquid may be a dimethyl sulfoxide-containing reaction liquid obtained in a step of synthesizing by oxidation or the like of dimethyl sulfide, a dimethyl sulfoxide-containing waste liquid used in a step of polymerization or spinning of a polymer such as polyacrylonitrile, cellulose, polyimide, polysulfone, or polyurethane, a dimethyl sulfoxide-containing waste liquid used as a stripping liquid for a photoresist that is an electronic material, a dimethyl sulfoxide-containing waste liquid used as a solvent for synthesizing a pharmaceutical or agrochemical, a dimethyl sulfoxide-containing waste liquid used as a removing and cleaning liquid for a lens mold or the like, a dimethyl sulfoxide-containing waste liquid used as a paint stripping liquid or the like.

EXAMPLES

Our methods will be specifically described by Examples hereinafter. Various kinds of measurement values used in the Examples and the like were measured by the following measurement methods.

(1) Dimethyl Sulfoxide Purity (area %)

Dimethyl Sulfoxide Purity was measured by gas chromatography under the following conditions:

Apparatus used: GC-2010 (FID) manufactured by Shimadzu Corporation

Column: DB-WAX, 0.25 mm×60 m, film thickness: 0.25 μm

Carrier gas: He: 165.7 kPa

Column temperature-increasing conditions: 35° C.→7° C./min→140° C.×10 min 15° C./min→250° C.×10 min Inlet temperature: 200° C.

Detector temperature: 250° C.

FID: Air: 400 ml/min, H2: 40 ml/min, Makeup: 30 ml/min

Split ratio: 14

Preparation of analysis sample: samples were filtered through a 0.5 μm PTFE syringe filter Amount of injection: 1.0 μl.

(2) Amount of Decomposition of Dimethyl Sulfoxide (area %)

Regarding a dimethyl sulfoxide-containing liquid before distillation (a charged liquid) and a mixed liquid prepared by mixing a distillate after the distillation (including a main distillate and, if any, an early distillate) and a residual liquid after the distillation (a post-distillation mixed liquid), dimethyl sulfoxide purities (area %) were measured in the same manner as in (1), and then, an amount of decomposition of dimethyl sulfoxide was obtained by the following calculation equation:

Amount of decomposition of dimethyl sulfoxide (area %)=purity in charged liquid (area %)−purity in post-distillation mixed liquid (area %).

(3) Amount of Additive

The amount of an additive before distillation is an amount of the additive with respect to 100 g of pure dimethyl sulfoxide in the dimethyl sulfoxide-containing liquid. In the gas chromatographic measurement of dimethyl sulfoxide in (1), neither water nor additive is detected. The amount of the pure dimethyl sulfoxide in the charged liquid was obtained by multiplying a value obtained by subtracting amounts of water and the additive from a total liquid amount by dimethyl sulfoxide purity in the charged liquid.

The amount of the additive after the distillation is an amount of the additive with respect to 100 g of pure dimethyl sulfoxide in the residual liquid after the distillation. The amount of the pure dimethyl sulfoxide in the residual liquid after the distillation was obtained by multiplying a value obtained by subtracting amounts of water and the additive from an amount of the residual liquid in the flask by dimethyl sulfoxide purity in the residual liquid.

(4) Additive Concentration Rate Between Before and After Distillation

Additive concentration rate between before and after the distillation was obtained by the following calculation equation:

Additive concentration rate between before and after distillation=(amount (g) of additive with respect to 100 g of pure dimethyl sulfoxide in residual liquid after distillation)/(amount (g) of additive with respect to 100 g of pure dimethyl sulfoxide in dimethyl sulfoxide-containing liquid before distillation).

Example 1

A 1-L four-necked flask equipped with a Dimroth condenser, a distillate receiver, a stirrer, and a thermometer necessary for simple distillation operation was charged with 720 g of dimethyl sulfoxide (purity: 99.997 area %) (pure dimethyl sulfoxide: 719.98 g), 80 g of ion-exchanged water, and, as an additive, 0.0072 g of sodium carbonate (0.001 g with respect to 100 g of the pure dimethyl sulfoxide). After substituting the inside of the flask with nitrogen, a rubber balloon filled with nitrogen was mounted at a top of the Dimroth condenser to seal the flask. The flask was heated in an oil bath maintained at 200° C., and a point in time when distillation started was considered to be a startup time. After collecting 100 ml containing water as an early distillate, a main distillation operation was performed in which the temperature of the oil bath was increased to 230° C., and distillate was collected until the amount of a residual liquid in the flask reached 8 g (the amount of water in the residual liquid: 0.0 g) and the amount of the additive after the distillation reached 0.09 g with respect to 100 g of the pure dimethyl sulfoxide. Heating time from the startup was 3 hours.

Dimethyl sulfoxide purity in the main distillate was 99.997 area % as shown in Table 1 so that high purity dimethyl sulfoxide was obtained.

Dimethyl sulfoxide purity in the residual liquid was 99.903 area % as shown in Table 1. Dimethyl sulfoxide was hardly decomposed even when heated for three hours at 147 to 170° C. (temperatures in the flask) in the early distillation operation and at 170 to 191° C. (temperatures in the flask) in the main distillation operation. Since the amount of the sodium carbonate in the residual liquid was 0.09 g with respect to 100 g of the pure dimethyl sulfoxide in the residual liquid, the sodium carbonate was concentrated to 90 times by the dimethyl sulfoxide distillation.

As shown in Table 1, dimethyl sulfoxide purity in a mixed liquid of the distillate after the distillation (the main distillate and the early distillate) and the residual liquid after the distillation (a post-distillation mixed liquid) was 99.994 area %, and the amount of decomposition was 0.003%, extremely small.

Example 2

A 1-L four-necked flask equipped with a Dimroth condenser, a distillate receiver, a stirrer, and a thermometer necessary for simple distillation operation was charged with 720 g of dimethyl sulfoxide (purity: 99.997 area %) (pure dimethyl sulfoxide: 719.98 g), 80 g of ion-exchanged water, and, as an additive, 0.72 g of sodium carbonate (0.1 g with respect to 100 g of the pure dimethyl sulfoxide). After substituting the inside of the flask with nitrogen, a rubber balloon filled with nitrogen was mounted at the top of the Dimroth condenser to seal the flask. The flask was heated in an oil bath maintained at 200° C., and a point in time when distillation started was considered to be a startup time. After collecting 100 ml containing water as an early distillate, a main distillation operation was performed in which the temperature of the oil bath was increased to 230° C., and distillate was collected until the amount of a residual liquid in the flask reached 72 g (the amount of water in the residual liquid: 0.0 g) and the amount of the additive after the distillation reached 1 g with respect to 100 g of the pure dimethyl sulfoxide. Heating time from the startup was 2.5 hours.

Dimethyl sulfoxide purity in the main distillate was 99.995 area % as shown in Table 1 so that high purity dimethyl sulfoxide was obtained.

Dimethyl sulfoxide purity in the residual liquid was 99.964 area % as shown in Table 1. Dimethyl sulfoxide was hardly decomposed even when heated for 2.5 hours at 147 to 170° C. (temperatures in the flask) in the early distillation operation and at 171 to 191° C. (temperatures in the flask) in the main distillation operation. Since the amount of the sodium carbonate in the residual liquid was 1 g with respect to 100 g of the pure dimethyl sulfoxide in the residual liquid, the sodium carbonate was concentrated to 10 times by the dimethyl sulfoxide distillation.

As shown in Table 1, dimethyl sulfoxide purity in a mixed liquid of the distillate after the distillation (the main distillate and the early distillate) and the residual liquid after the distillation (a post-distillation mixed liquid) was 99.991 area %, and the amount of decomposition was 0.006%, extremely small.

Example 3

A 1-L four-necked flask equipped with a Dimroth condenser, a distillate receiver, a stirrer, and a thermometer necessary for simple distillation operation was charged with 720 g of dimethyl sulfoxide (purity: 99.997 area %) (pure dimethyl sulfoxide: 719.98 g), 80 g of ion-exchanged water, and, as an additive, 7.2 g of sodium carbonate (1 g with respect to 100 g of the pure dimethyl sulfoxide). After substituting the inside of the flask with nitrogen, a rubber balloon filled with nitrogen was mounted at the top of the Dimroth condenser to seal the flask. The flask was heated in an oil bath maintained at 200° C., and a point in time when distillation started was considered to be a startup time. After collecting 100 ml containing water as an early distillate, a main distillation operation was performed in which the temperature of the oil bath was increased to 230° C., and distillate was collected until the amount of a residual liquid in the flask reached 16 g (the amount of water in the residual liquid: 0.0 g) and the amount of the additive after the distillation reached 82 g with respect to 100 g of the pure dimethyl sulfoxide. Heating time from the startup was 3 hours.

Dimethyl sulfoxide purity in the main distillation was 99.994 area % as shown in Table 1 so that high purity dimethyl sulfoxide was obtained.

Dimethyl sulfoxide purity in the residual liquid was 99.892 area % as shown in Table 1. Dimethyl sulfoxide was hardly decomposed even when heated for 3 hours at 147 to 170° C. (temperatures in the flask) in the early distillation operation and at 170 to 191° C. (temperatures in the flask) in the main distillation operation. Since the amount of the sodium carbonate in the residual liquid was 82 g with respect to 100 g of the pure dimethyl sulfoxide in the residual liquid, the sodium carbonate was concentrated to 82 times by the dimethyl sulfoxide distillation.

As shown in Table 1, dimethyl sulfoxide purity in a mixed liquid of the distillate after the distillation (the main distillate and the early distillate) and the residual liquid after the distillation (a post-distillation mixed liquid) was 99.992 area %, and the amount of decomposition was 0.005%, extremely small.

Comparative Example 1

A 1-L four-necked flask equipped with a Dimroth condenser, a distillate receiver, a stirrer, and a thermometer necessary for simple distillation operation was charged with 720 g of dimethyl sulfoxide (purity: 99.997 area %) (pure dimethyl sulfoxide: 719.98 g) and 80 g of ion-exchanged water without adding any additive. After substituting the inside of the flask with nitrogen, a rubber balloon filled with nitrogen was mounted at the top of the Dimroth condenser to seal the flask. The flask was heated in an oil bath maintained at 200° C., and a point in time when distillation started was considered to be a startup time. After collecting 100 ml containing water as an early distillate, a main distillation operation was performed in which the temperature of the oil bath was increased to 230° C., and distillate was collected until the amount of a residual liquid in the flask reached 11 g (the amount of water in the residual liquid: 0.0 g). Heating time from the startup was 3 hours.

Dimethyl sulfoxide purity in the main distillate was 99.988 area % as shown in Table 1 which indicated reduced dimethyl sulfoxide purity.

Dimethyl sulfoxide purity in the residual liquid was 99.922 area % as shown in Table 1. As shown in Table 1, dimethyl sulfoxide purity in a mixed liquid of the distillate after the distillation (the main distillate and the early distillate) and the residual liquid after the distillation (a post-distillation mixed liquid) was 99.987 area %, and the amount of decomposition was 0.010% that was larger than Examples from 1 to 3.

Comparative Example 2

A 1-L four-necked flask equipped with a Dimroth condenser, a distillate receiver, a stirrer, and a thermometer necessary for simple distillation operation was charged with 720 g of dimethyl sulfoxide (purity: 99.997 area %) (pure dimethyl sulfoxide: 719.98 g), 80 g of ion-exchanged water, and as an additive, 0.144 g of sodium hydroxide (0.02 g with respect to 100 g of the pure dimethyl sulfoxide). After substituting the inside of the flask with nitrogen, a rubber balloon filled with nitrogen was mounted at the top of the Dimroth condenser to seal the flask. The flask was heated in an oil bath maintained at 200° C., and a point in time when distillation started was considered to be a startup time. After collecting 100 ml containing water as an early distillate, a main distillation operation was performed in which the temperature of the oil bath was increased to 230° C., and distillate was collected until the amount of a residual liquid in the flask reached 7 g (the amount of water in the residual liquid: 0.0 g) and the amount of the additive after the distillation reached 2 g with respect to 100 g of the pure dimethyl sulfoxide. Heating time from the startup was 3 hours.

Dimethyl sulfoxide purity in the main distillate was 99.960 area % as shown in Table 1 which indicated reduced dimethyl sulfoxide purity.

Dimethyl sulfoxide purity in the residual liquid was 99.568 area % as shown in Table 1. Dimethyl sulfoxide was slightly decomposed when heated for 3 hours at 147 to 170° C. (temperatures in the flask) in the early distillation operation and at 170 to 191° C. (temperatures in the flask) in the main distillation operation.

As shown in Table 1, dimethyl sulfoxide purity in a mixed liquid of the distillate after the distillation (the main distillate and the early distillate) and the residual liquid after the distillation (a post-distillation mixed liquid) was 99.956 area %, and the amount of decomposition was 0.041% that was larger than Examples from 1 to 3.

Comparative Example 3

A 1-L four-necked flask equipped with a Dimroth condenser, a distillate receiver, a stirrer, and a thermometer necessary for simple distillation operation was charged with 720 g of dimethyl sulfoxide (purity: 99.997 area %) (pure dimethyl sulfoxide: 719.98 g), 80 g of ion-exchanged water, and as an additive, 7.2 g of potassium carbonate (1 g with respect to 100 g of the pure dimethyl sulfoxide). After substituting the inside of the flask with nitrogen, a rubber balloon filled with nitrogen was mounted at the top of the Dimroth condenser to seal the flask. The flask was heated in an oil bath maintained at 200° C., and a point in time when distillation started was considered to be a startup time. After collecting 100 ml containing water as an early distillate, a main distillation operation was performed in which the temperature of the oil bath was increased to 230° C., and distillate was collected until the amount of a residual liquid in the flask reached 18 g (the amount of water in the residual liquid: 0.0 g) and the amount of the additive after the distillation reached 67 g with respect to 100 g of the pure dimethyl sulfoxide. Heating time from the startup was 3 hours.

Dimethyl sulfoxide purity in the main distillate was 99.984 area % as shown in Table 1 which indicated reduced dimethyl sulfoxide purity.

Dimethyl sulfoxide purity in the residual liquid was 99.617 area % as shown in Table 1. Dimethyl sulfoxide was slightly decomposed when heated for 3 hours at 147 to 170° C. (temperatures in the flask) in the early distillation operation and at 170 to 191° C. (temperatures in the flask) in the main distillation operation.

As shown in Table 1, dimethyl sulfoxide purity in a mixed liquid of the distillate after the distillation (the main distillate and the early distillate) and the residual liquid after the distillation (a post-distillation mixed liquid) was 99.975 area %, and the amount of decomposition was 0.022% that was larger than Examples from 1 to 3.

Comparative Example 4

A 1-L four-necked flask equipped with a Dimroth condenser, a distillate receiver, a stirrer, and a thermometer necessary for simple distillation operation was charged with 720 g of dimethyl sulfoxide (purity: 99.997 area %) (pure dimethyl sulfoxide: 719.98 g), 80 g of ion-exchanged water, and as an additive, 0.216 g of sodium carbonate (0.03 g with respect to 100 g of the pure dimethyl sulfoxide). Without performing nitrogen substitution, a rubber balloon filled with air was mounted at the top of the Dimroth condenser to seal the inside of the flask in the air. The flask was heated in an oil bath maintained at 200° C., in which a point in time when distillation started was considered to be a startup time. After collecting 100 ml containing water as an early distillate, a main distillation operation was performed in which the temperature of the oil bath was increased to 230° C., and distillate was collected until the amount of a residual liquid in the flask reached 22 g (the amount of water in the residual liquid: 0.0 g) and the amount of the additive after the distillation reached 0.99 g with respect to 100 g of the pure dimethyl sulfoxide. Heating time from the startup was 3 hours.

Dimethyl sulfoxide purity in the main distillate was 99.982 area % as shown in Table 1 which indicated reduced dimethyl sulfoxide purity.

Dimethyl sulfoxide purity in the residual liquid was 99.844 area % as shown in Table 1. Dimethyl sulfoxide was slightly decomposed when heated for 3 hours at 147 to 170° C. (temperatures in the flask) in the early distillation operation and at 171 to 193° C. (temperatures in the flask) in the main distillation operation.

As shown in Table 1, dimethyl sulfoxide purity in a mixed liquid of the distillate after the distillation (the main distillate and the early distillate) and the residual liquid after the distillation (a post-distillation mixed liquid) was 99.978 area %, and the amount of decomposition was 0.019% that was larger than Examples from 1 to 3.

balloon filled with nitrogen was mounted at the top of the Dimroth condenser to seal the flask. The flask was heated in an oil bath maintained at from 145 to 191° C. under a pressure of from 20 to 720 Torr, and a point in time when distillation started was considered to be a startup time. After collecting 2289 g containing water as an early distillate, a main distillation operation was performed in which the flask was heated in an oil bath at from 153 to 192° C. under a pressure of 20 Torr, and main distillate during a time when the temperature in the flask ranged from 110 to 112° C. was collected until the amount of a residual liquid in the flask reached 688 g (the amount of water in the residual liquid: 0.0 g) and the amount of the additive after the distillation reached 0.2 g with respect to 100 g of the pure dimethyl sulfoxide. Heating time from the startup was 12 hours.

Dimethyl sulfoxide purity in the main distillate was 99.999 area % as shown in Table 2 so that high purity dimethyl sulfoxide was obtained.

TABLE 1

| | | | Charged liquid | | | Main distillate | | Residual liquid | | Additive concentration rate | Purity in post-distillation mixed liquid (area %) | Amount of decomposition (area %) |
|---|---|---|---|---|---|---|---|---|---|---|---|---|
| | Additive | Atmosphere in system | Dimethyl sulfoxide purity (area %) | Amount of additive (g) | Amount of water (g) | Pressure | Temperatures in flask (° C.) | Dimethyl sulfoxide purity (area %) | Dimethyl sulfoxide purity (area %) | Amount of additive (g) | | | |
| Ex 1 | Sodium carbonate | Nitrogen | 99.997 | 0.001 | 11 | Atmospheric Pressure | 170-191 | 99.997 | 99.903 | 0.09 | 90 | 99.994 | 0.003 |
| Ex 2 | Sodium carbonate | Nitrogen | 99.997 | 0.1 | 11 | Atmospheric Pressure | 171-191 | 99.995 | 99.964 | 1 | 10 | 99.991 | 0.006 |
| Ex 3 | Sodium carbonate | Nitrogen | 99.997 | 1 | 11 | Atmospheric Pressure | 170-191 | 99.994 | 99.892 | 82 | 82 | 99.992 | 0.005 |
| Com Ex 1 | None | Nitrogen | 99.997 | — | 11 | Atmospheric Pressure | 171-192 | 99.988 | 99.922 | — | — | 99.987 | 0.010 |
| Com Ex 2 | Sodium hydroxide | Nitrogen | 99.997 | 0.02 | 11 | Atmospheric Pressure | 170-191 | 99.960 | 99.568 | 2 | 100 | 99.956 | 0.041 |
| Com Ex 3 | Potassium carbonate | Nitrogen | 99.997 | 1 | 11 | Atmospheric Pressure | 170-191 | 99.984 | 99.617 | 67 | 67 | 99.975 | 0.022 |
| Com Ex 4 | Sodium carbonate | Air | 99.997 | 0.03 | 11 | Atmospheric Pressure | 171-193 | 99.982 | 99.844 | 0.99 | 33 | 99.978 | 0.019 |

Amount of additive is the amount of an additive with respect to 100 g of the pure dimethyl sulfoxide in the liquid.
Amount of water in charged liquid is the amount of water with respect to 100 g of the pure dimethyl sulfoxide in the liquid.

In Examples from 1 to 3, high purity dimethyl sulfoxide was obtained as the main distillates. On the other hand, the dimethyl sulfoxide purities in the main distillates obtained in Comparative Examples from 1 to 4 were lower than those in Examples from 1 to 3.

Example 4

A 10-L four-necked flask equipped with a distillation column filled with a structured packing, a distillate receiver, a stirrer, a thermometer, and a Dimroth condenser provided at the top of the distillation column was charged with 4830 g of dimethyl sulfoxide (purity: 99.998 area %) (pure dimethyl sulfoxide: 4829.9 g), 1998 g of ion-exchanged water, and, as an additive, 1.4 g of sodium carbonate (0.03 g with respect to 100 g of the pure dimethyl sulfoxide). After substituting the inside of the flask with nitrogen, a rubber Dimethyl sulfoxide purity in the residual liquid was 99.975 area % as shown in Table 2. Even when heated, dimethyl sulfoxide was hardly decomposed. Since the amount of the sodium carbonate in the residual liquid was 0.2 g with respect to 100 g of the pure dimethyl sulfoxide in the residual liquid, the sodium carbonate was concentrated to 7 times by the dimethyl sulfoxide distillation.

As shown in Table 2, dimethyl sulfoxide purity in a mixed liquid of the distillate after the distillation (the main distillate) and the residual liquid after the distillation (a post-distillation mixed liquid) was 99.992 area %, and the amount of decomposition was 0.006%, extremely small. In Example 4, high purity dimethyl sulfoxide was obtained as the main distillate.

TABLE 2

| | Additive | Charged liquid | | | Pressure | Main distillate | | Residual liquid | | Additive concentration rate | Purity in post-distillation mixed liquid (area %) | Amount of decomposition (area %) |
| | | Dimethyl sulfoxide purity (area %) | Amount of additive (g) | Amount of water (g) | | Temperatures in flask (° C.) | Dimethyl sulfoxide purity (area %) | Dimethyl sulfoxide purity (area %) | Amount of additive (g) | | | |
|---|---|---|---|---|---|---|---|---|---|---|---|---|
| Ex 4 | Sodium carbonate | 99.998 | 0.03 | 41 | Reduced pressure | 110-112 | 99.999 | 99.975 | 0.2 | 7 | 99.992 | 0.006 |

Amount of additive is the amount of an additive with respect to 100 g of the pure dimethyl sulfoxide in the liquid.
Amount of water in charged liquid is the amount of water with respect to 100 g of the pure dimethyl sulfoxide in the liquid.

Example 5

A 1-L four-necked flask equipped with a Dimroth condenser, a distillate receiver, a stirrer, and a thermometer necessary for simple distillation operation was charged with 400 g of dimethyl sulfoxide (purity: 99.995 area %) (pure dimethyl sulfoxide: 399.98 g), 400 g of ion-exchanged water, and as an additive, 0.004 g of sodium carbonate (0.001 g with respect to 100 g of the pure dimethyl sulfoxide). After substituting the inside of the flask with nitrogen, a rubber balloon filled with nitrogen was mounted at the top of the Dimroth condenser to seal the flask. The flask was heated in an oil bath maintained at 220° C., and a point in time when distillation started was considered to be a startup time. After collecting 500 ml containing water as an early distillate, a main distillation operation was performed in which the temperature of the oil bath was increased to 230° C., and distillate was collected until the amount of a residual liquid in the flask reached 9 g (the amount of water in the residual liquid: 0.0 g) and the amount of the additive after the distillation reached 0.044 g with respect to 100 g of the pure dimethyl sulfoxide. Heating time from the startup was 3 hours.

Dimethyl sulfoxide purity in the main distillate was 99.994 area % as shown in Table 3 so that high purity dimethyl sulfoxide was obtained.

Dimethyl sulfoxide purity in the residual liquid was 99.932 area % as shown in Table 3. Dimethyl sulfoxide was hardly decomposed even when heated for 3 hours at 108 to 192° C. (temperatures in the flask) in the early distillation operation and at 192 to 193° C. (temperatures in the flask) in the main distillation operation. Since the amount of the sodium carbonate in the residual liquid was 0.044 g with respect to 100 g of the pure dimethyl sulfoxide in the residual liquid, the sodium carbonate was concentrated to 44 times by the dimethyl sulfoxide distillation.

As shown in Table 3, dimethyl sulfoxide purity in a mixed liquid of the distillate after the distillation (the main distillate and the early distillate) and the residual liquid after the distillation (a post-distillation mixed liquid) was 99.992 area %, and the amount of decomposition was 0.003%, extremely small.

Example 6

Example 6 was performed in the same manner as Example 5 except that the amount of sodium carbonate added was changed to 0.024 g (0.006 g with respect to 100 g of the pure dimethyl sulfoxide), and distillate was collected until the amount of a residual liquid in the flask reached 32 g (the amount of water in the residual liquid: 0.0 g) and the amount of the additive after the distillation reached 0.075 g with respect to 100 g of the pure dimethyl sulfoxide. Heating time from the startup was 2.5 hours.

Dimethyl sulfoxide purity in the main distillate was 99.992 area % as shown in Table 3 so that high purity dimethyl sulfoxide was obtained.

Dimethyl sulfoxide purity in the residual liquid was 99.964 area % as shown in Table 3. Dimethyl sulfoxide was hardly decomposed even when heated for 2.5 hours at 108 to 192° C. (temperatures in the flask) in the early distillation operation and at 192 to 193° C. (temperatures in the flask) in the main distillation operation. Since the amount of the sodium carbonate in the residual liquid was 0.075 g with respect to 100 g of the pure dimethyl sulfoxide in the residual liquid, the sodium carbonate was concentrated to 13 times by the dimethyl sulfoxide distillation.

As shown in Table 3, dimethyl sulfoxide purity in a mixed liquid of the distillate after the distillation (the main distillate and the early distillate) and the residual liquid after the distillation (a post-distillation mixed liquid) was 99.988 area %, and the amount of decomposition was 0.007%, extremely small.

Example 7

Example 7 was performed in the same manner as Example 5 except that the amount of sodium carbonate added was changed to 0.08 g (0.02 g with respect to 100 g of pure dimethyl sulfoxide), and distillate was collected until the amount of a residual liquid in the flask reached 34 g (the amount of water in the residual liquid: 0.0 g) and the amount of the additive after the distillation reached 0.24 g with respect to 100 g of the pure dimethyl sulfoxide. Heating time from the startup was 2.5 hours.

Dimethyl sulfoxide purity in the main distillate was 99.991 area % as shown in Table 3 so that high purity dimethyl sulfoxide was obtained.

Dimethyl sulfoxide purity in the residual liquid was 99.965 area % as shown in Table 3. Dimethyl sulfoxide was hardly decomposed even when heated for 2.5 hours at 108 to 192° C. (temperatures in the flask) in the early distillation operation and at 192 to 193° C. (temperatures in the flask) in the main distillation operation. Since the amount of the sodium carbonate in the residual liquid was 0.24 g with respect to 100 g of the pure dimethyl sulfoxide in the residual liquid, the sodium carbonate was concentrated to 12 times by the dimethyl sulfoxide distillation.

As shown in Table 3, dimethyl sulfoxide purity in a mixed liquid of the distillate after the distillation (the main distillate and the early distillate) and the residual liquid after the distillation (a post-distillation mixed liquid) was 99.988 area %, and the amount of decomposition was 0.007%, extremely small.

Example 8

Example 8 was performed in the same manner as Example 5 except that the amount of sodium carbonate added was changed to 0.4 g (0.1 g with respect to 100 g of pure dimethyl sulfoxide), and distillate was collected until the amount of a residual liquid in the flask reached 28 g (the amount of water in the residual liquid: 0.0 g) and the amount of the additive after the distillation reached 1.4 g with respect to 100 g of the pure dimethyl sulfoxide. Heating time from the startup was 2.5 hours.

Dimethyl sulfoxide purity in the main distillate was 99.991 area % as shown in Table 3 so that high purity dimethyl sulfoxide was obtained.

Dimethyl sulfoxide purity in the residual liquid was 99.956 area % as shown in Table 3. Dimethyl sulfoxide was hardly decomposed even when heated for 2.5 hours at 108 to 192° C. (temperatures in the flask) in the early distillation operation and at 192 to 193° C. (temperatures in the flask) in the main distillation operation. Since the amount of the sodium carbonate in the residual liquid was 1.4 g with respect to 100 g of the pure dimethyl sulfoxide in the residual liquid, the sodium carbonate was concentrated to 14 times by the dimethyl sulfoxide distillation.

As shown in Table 3, dimethyl sulfoxide purity in a mixed liquid of the distillate after the distillation (the main distillate and the early distillate) and the residual liquid after the distillation (a post-distillation mixed liquid) was 99.987 area %, and the amount of decomposition was 0.008%, extremely small.

Example 9

Example 9 was performed in the same manner as Example 5 except that the amount of sodium carbonate added was changed to 4 g (1 g with respect to 100 g of pure dimethyl sulfoxide), and distillate was collected until the amount of a residual liquid in the flask reached 42 g (the amount of water in the residual liquid: 0.0 g) and the amount of the additive after the distillation reached 11 g with respect to 100 g of the pure dimethyl sulfoxide. Heating time from the startup was 2.5 hours.

Dimethyl sulfoxide purity in the main distillate was 99.995 area % as shown in Table 3 so that high purity dimethyl sulfoxide was obtained.

Dimethyl sulfoxide purity in the residual liquid was 99.985 area % as shown in Table 3. Dimethyl sulfoxide was hardly decomposed even when heated for 2.5 hours at 108 to 192° C. (temperatures in the flask) in the early distillation operation and at 192 to 193° C. (temperatures in the flask) in the main distillation operation. Since the amount of the sodium carbonate in the residual liquid was 11 g with respect to 100 g of the pure dimethyl sulfoxide in the residual liquid, the sodium carbonate was concentrated to 11 times by the dimethyl sulfoxide distillation.

As shown in Table 3, dimethyl sulfoxide purity in a mixed liquid of the distillate after the distillation (the main distillate and the early distillate) and the residual liquid after the distillation (a post-distillation mixed liquid) was 99.992 area %, and the amount of decomposition was 0.003%, extremely small.

Example 10

Example 10 was performed in the same manner as Example 5 except that the amount of sodium carbonate added was changed to 4 g (1 g with respect to 100 g of pure dimethyl sulfoxide), and distillate was collected until the amount of a residual liquid in the flask reached 17 g (the amount of water in the residual liquid: 0.0 g) and the amount of the additive after the distillation reached 31 g with respect to 100 g of the pure dimethyl sulfoxide. Heating time from the startup was 3 hours.

Dimethyl sulfoxide purity in the main distillate was 99.994 area % as shown in Table 3 so that high purity dimethyl sulfoxide was obtained.

Dimethyl sulfoxide purity in the residual liquid was 99.968 area % as shown in Table 3. Dimethyl sulfoxide was hardly decomposed even when heated for 3 hours at 108 to 192° C. (temperatures in the flask) in the early distillation operation and at 192 to 193° C. (temperatures in the flask) in the main distillation operation. Since the amount of the sodium carbonate in the residual liquid was 31 g with respect to 100 g of the pure dimethyl sulfoxide in the residual liquid, the sodium carbonate was concentrated to 31 times by the dimethyl sulfoxide distillation.

As shown in Table 3, dimethyl sulfoxide purity in a mixed liquid of the distillate after the distillation (the main distillate and the early distillate) and the residual liquid after the distillation (a post-distillation mixed liquid) was 99.992 area %, and the amount of decomposition was 0.003%, extremely small.

Comparative Example 5

Comparative Example 5 was performed in the same manner as Example 5 except for not adding sodium carbonate, and distillate was collected until the amount of a residual liquid in the flask reached 23 g (the amount of water in the residual liquid: 0.0 g). Heating time from the startup was 3 hours.

Dimethyl sulfoxide purity in the main distillate was 99.978 area % as shown in Table 3 which indicated reduced dimethyl sulfoxide purity.

Dimethyl sulfoxide purity in the residual liquid was 99.961 area % as shown in Table 3. Dimethyl sulfoxide was slightly decomposed when heated for 3 hours at 108 to 192° C. (temperatures in the flask) in the early distillation operation and at 192 to 193° C. (temperatures in the flask) in the main distillation operation. As shown in Table 3, dimethyl sulfoxide purity in a mixed liquid of the distillate after the distillation (the main distillate and the early distillate) and the residual liquid after the distillation (a post-distillation mixed liquid) was 99.979 area %, and the amount of decomposition was 0.016% that was larger than Examples 5 to 10. Additionally, as a decomposition product of the dimethyl sulfoxide, a small amount of polymer, which seemed to be polyacetal, was deposited on the tool after the distillation.

Comparative Example 6

Comparative Example 6 was performed in the same manner as Example 5 except that the kind of the additive was changed to sodium hydroxide and the amount of the additive added was changed to 0.08 g (0.02 g with respect to 100 g of pure dimethyl sulfoxide), and distillate was collected until the amount of a residual liquid in the flask reached 35 g (the amount of water in the residual liquid: 0.0 g) and the amount of the additive after the distillation reached 0.23 g with respect to 100 g of the pure dimethyl sulfoxide. Heating time from the startup was 2.5 hours.

Dimethyl sulfoxide purity in the main distillate was 99.980 area % as shown in Table 3 which indicated reduced dimethyl sulfoxide purity.

Dimethyl sulfoxide purity in the residual liquid was 99.926 area % as shown in Table 3. Dimethyl sulfoxide was late) and the residual liquid after the distillation (a post-distillation mixed liquid) was 99.963 area %, and the amount of decomposition was 0.032% that was larger than Examples from 5 to 10.

TABLE 3

|  |  | Charged liquid | | | Main distillate | | | Residual liquid | | | Purity in post-distillation mixed liquid (area %) | Amount of decomposition (area %) |
| --- | --- | --- | --- | --- | --- | --- | --- | --- | --- | --- | --- | --- |
|  | Additive | Dimethyl sulfoxide purity (area %) | Amount of additive (g) | Amount of water (g) | Pressure | Temperatures in flask (° C.) | Dimethyl sulfoxide purity (area %) | Dimethyl sulfoxide purity (area %) | Amount of additive (g) | Additive concentration rate |  |  |
| Ex 5 | Sodium carbonate | 99.995 | 0.001 | 100 | Atmospheric pressure | 192-193 | 99.994 | 99.932 | 0.044 | 44 | 99.992 | 0.003 |
| Ex 6 | Sodium carbonate | 99.995 | 0.006 | 100 | Atmospheric pressure | 192-193 | 99.992 | 99.964 | 0.075 | 13 | 99.988 | 0.007 |
| Ex 7 | Sodium carbonate | 99.995 | 0.02 | 100 | Atmospheric pressure | 192-193 | 99.991 | 99.965 | 0.24 | 12 | 99.988 | 0.007 |
| Ex 8 | Sodium carbonate | 99.995 | 0.1 | 100 | Atmospheric pressure | 192-193 | 99.991 | 99.956 | 1.4 | 14 | 99.987 | 0.008 |
| Ex 9 | Sodium carbonate | 99.995 | 1 | 100 | Atmospheric pressure | 192-193 | 99.995 | 99.985 | 11 | 11 | 99.992 | 0.003 |
| Ex 10 | Sodium carbonate | 99.995 | 1 | 100 | Atmospheric pressure | 192-193 | 99.994 | 99.968 | 31 | 31 | 99.992 | 0.003 |
| Com Ex 5 | None | 99.995 | — | 100 | Atmospheric pressure | 192-193 | 99.978 | 99.961 | — | — | 99.979 | 0.016 |
| Com Ex 6 | Sodium hydroxide | 99.995 | 0.02 | 100 | Atmospheric pressure | 192-193 | 99.980 | 99.926 | 0.23 | 12 | 99.971 | 0.024 |
| Com Ex 7 | Sodium hydroxide | 99.995 | 0.1 | 100 | Atmospheric pressure | 192-193 | 99.972 | 99.910 | 1.3 | 13 | 99.963 | 0.032 |

Amount of additive is the amount of an additive with respect to 100 g of the pure dimethyl sulfoxide in the liquid.
Amount of water in charged liquid is the amount of water with respect to 100 g of the pure dimethyl sulfoxide in the liquid.

slightly decomposed when heated for 2.5 hours at 108 to 192° C. (temperatures in the flask) in the early distillation operation and at 192 to 193° C. (temperatures in the flask) in the main distillation operation. As shown in Table 3, dimethyl sulfoxide purity in a mixed liquid of the distillate after the distillation (the main distillate and the early distillate) and the residual liquid after the distillation (a post-distillation mixed liquid) was 99.971 area %, and the amount of decomposition was 0.024% that was larger than Examples from 5 to 10.

Comparative Example 7

Comparative Example 7 was performed in the same manner as Example 5 except that the kind of the additive was changed to sodium hydroxide and the amount of the additive added was changed to 0.4 g (0.1 g with respect to 100 g of pure dimethyl sulfoxide), and distillate was collected until the amount of a residual liquid in the flask reached 32 g (the amount of water in the residual liquid: 0.0 g) and the amount of the additive after the distillation reached 1.3 g with respect to 100 g of the pure dimethyl sulfoxide. Heating time from the startup was 2.5 hours.

Dimethyl sulfoxide purity in the main distillate was 99.972 area % as shown in Table 3 which indicated reduced dimethyl sulfoxide purity.

Dimethyl sulfoxide purity in the residual liquid was 99.910 area % as shown in Table 3. Dimethyl sulfoxide was slightly decomposed when heated for 2.5 hours at 108 to 192° C. (temperatures in the flask) in the early distillation operation and at 192 to 193° C. (temperatures in the flask) in the main distillation operation. As shown in Table 3, dimethyl sulfoxide purity in a mixed liquid of the distillate after the distillation (the main distillate and the early distillate) and the residual liquid after the distillation (a post-distillation mixed liquid) was 99.963 area %, and the amount of decomposition was 0.032% that was larger than Examples from 5 to 10.

In Examples 5 to 10, high purity dimethyl sulfoxide was obtained as the main distillates. On the other hand, the dimethyl sulfoxide purities in the main distillates obtained in Comparative Examples 5 to 7 were lower than those in Examples 5 to 10.

Example 11

A 1-L four-necked flask equipped with a Dimroth condenser, a distillate receiver, a stirrer, and a thermometer necessary for simple distillation operation was charged with 720 g of dimethyl sulfoxide (purity: 99.995 area %) (pure dimethyl sulfoxide: 719.96 g) and, as an additive, 7.2 g of sodium carbonate (1 g with respect to 100 g of the pure dimethyl sulfoxide). After substituting the inside of the flask with nitrogen, a rubber balloon filled with nitrogen was mounted at the top of the Dimroth condenser to seal the flask. The flask was heated in an oil bath maintained at 220° C., and a point in time when distillation started was considered to be a startup time. Distillate was collected until the amount of a residual liquid in the flask reached 56 g (the amount of water in the residual liquid: 0.0 g) and the amount of the additive after the distillation reached 15 g with respect to 100 g of the pure dimethyl sulfoxide. Heating time from the startup was 2.5 hours.

Dimethyl sulfoxide purity in the main distillate was 99.990 area % as shown in Table 4 so that high purity dimethyl sulfoxide was obtained.

Dimethyl sulfoxide purity in the residual liquid was 99.930 area % as shown in Table 4. Dimethyl sulfoxide was hardly decomposed even when heated for 2.5 hours at 192 to 193° C. (temperatures in the flask). Since the amount of the sodium carbonate in the residual liquid was 15 g with respect to 100 g of the pure dimethyl sulfoxide in the residual liquid, the sodium carbonate was concentrated to 15 times by the dimethyl sulfoxide distillation.

As shown in Table 4, dimethyl sulfoxide purity in a mixed liquid of the distillate after the distillation (the main distillate) and the residual liquid after the distillation (a post-distillation mixed liquid) was 99.986 area %, and the amount of decomposition was 0.009%, extremely small.

Example 12

A 1-L four-necked flask equipped with a Dimroth condenser, a distillate receiver, a stirrer, and a thermometer necessary for simple distillation operation was charged with 720 g of dimethyl sulfoxide (purity: 99.995 area %) (pure dimethyl sulfoxide: 719.96 g). Next, as an additive, 7.2 g of sodium carbonate monohydrate (0.86 g of the sodium carbonate with respect to 100 g of the pure dimethyl sulfoxide) was charged therein. After substituting the inside of the flask with nitrogen, a rubber balloon filled with nitrogen was mounted at the top of the Dimroth condenser to seal the flask. The flask was heated in an oil bath maintained at 220° C., and a point in time when distillation started was considered to be a startup time. After collecting 12 ml containing water as an early distillate, a main distillation operation was performed in which the temperature of the oil bath was increased to 230° C., and distillate was collected until the amount of a residual liquid in the flask reached 61 g (the amount of water in the residual liquid: 0.0 g) and the amount of the sodium carbonate after the distillation reached 11.4 g with respect to 100 g of the pure dimethyl sulfoxide. Heating time from the startup was 2.5 hours.

Dimethyl sulfoxide purity in the main distillate was 99.990 area % as shown in Table 4 so that high purity dimethyl sulfoxide was obtained.

Dimethyl sulfoxide purity in the residual liquid was 99.936 area % as shown in Table 4. Dimethyl sulfoxide was hardly decomposed even when heated for 2.5 hours at 191 to 192° C. (temperatures in the flask) in the early distillation operation and at 192 to 193° C. (temperatures in the flask) in the main distillation operation. Since the amount of the sodium carbonate in the residual liquid was 11.4 g with respect to 100 g of the pure dimethyl sulfoxide in the residual liquid, the sodium carbonate was concentrated to 13 times by the dimethyl sulfoxide distillation.

As shown in Table 4, dimethyl sulfoxide purity in a mixed liquid of the distillate after the distillation (the main distillate and the early distillate) and the residual liquid after the distillation (a post-distillation mixed liquid) was 99.986 area %, and the amount of decomposition was 0.009%, extremely small.

Example 13

A 1-L four-necked flask equipped with a Dimroth condenser, a distillate receiver, a stirrer, and a thermometer necessary for simple distillation operation was charged with 720 g of dimethyl sulfoxide (purity: 99.995 area %) (pure dimethyl sulfoxide: 719.96 g). Next, as an additive, 7.2 g of sodium carbonate decahydrate (0.37 g of the sodium carbonate with respect to 100 g of the pure dimethyl sulfoxide) was charged therein. After substituting the inside of the flask with nitrogen, a rubber balloon filled with nitrogen was mounted at the top of the Dimroth condenser to seal the flask. The flask was heated in an oil bath maintained at 220° C., and a point in time when distillation started was considered to be a startup time. After collecting 16 ml containing water as an early distillate, a main distillation operation was performed in which the temperature of the oil bath was increased to 230° C., and distillate was collected until the amount of a residual liquid in the flask reached 82 g (the amount of water in the residual liquid: 0.0 g) and the amount of the sodium carbonate after the distillation reached 3.4 g with respect to 100 g of the pure dimethyl sulfoxide. Heating time from the startup was 2.8 hours.

Dimethyl sulfoxide purity in the main distillate was 99.990 area % as shown in Table 4 so that high purity dimethyl sulfoxide was obtained.

Dimethyl sulfoxide purity in the residual liquid was 99.951 area % as shown in Table 4. Dimethyl sulfoxide was hardly decomposed even when heated for 2.8 hours at 187 to 190° C. (temperatures in the flask) in the early distillation operation and at 191 to 193° C. (temperatures in the flask) in the main distillation operation. Since the amount of the sodium carbonate in the residual liquid was 3.4 g with respect to 100 g of the pure dimethyl sulfoxide in the residual liquid, the sodium carbonate was concentrated to 9 times by the dimethyl sulfoxide distillation.

As shown in Table 4, dimethyl sulfoxide purity in a mixed liquid of the distillate after the distillation (the main distillate and the early distillate) and the residual liquid after the distillation (a post-distillation mixed liquid) was 99.986 area %, and the amount of decomposition was 0.009%, extremely small.

Example 14

A 1-L four-necked flask equipped with a Dimroth condenser, a distillate receiver, a stirrer, and a thermometer necessary for simple distillation operation was charged with 720 g of dimethyl sulfoxide (purity: 99.996 area %) (pure dimethyl sulfoxide: 759.97 g). Next, as an additive, there was charged a sodium carbonate aqueous solution prepared by dissolving 7.2 g of sodium carbonate (1 g with respect to 100 g of the pure dimethyl sulfoxide) in 40 g of ion-exchanged water. After substituting the inside of the flask with nitrogen, a rubber balloon filled with nitrogen was mounted at the top of the Dimroth condenser to seal the flask. The flask was heated in an oil bath maintained at 220° C., and a point in time when distillation started was considered to be a startup time. After collecting 140 ml containing water as an early distillate, a main distillation operation was performed in which the temperature of the oil bath was increased to 230° C., and distillate was collected until the amount of a residual liquid in the flask reached 56 g (the amount of water in the residual liquid: 0.0 g) and the amount of the sodium carbonate after the distillation reached 15 g with respect to 100 g of the pure dimethyl sulfoxide. Heating time from the startup was 2 hours.

Dimethyl sulfoxide purity in the main distillate was 99.995 area % as shown in Table 4 so that high purity dimethyl sulfoxide was obtained.

Dimethyl sulfoxide purity in the residual liquid was 99.956 area % as shown in Table 4. Dimethyl sulfoxide was hardly decomposed even when heated for 2 hours at 162 to 191° C. (temperatures in the flask) in the early distillation operation and at 192 to 193° C. (temperatures in the flask) in the main distillation operation. Since the amount of the sodium carbonate in the residual liquid was 15 g with respect to 100 g of the pure dimethyl sulfoxide in the residual liquid, the sodium carbonate was concentrated to 15 times by the dimethyl sulfoxide distillation.

As shown in Table 4, dimethyl sulfoxide purity in a mixed liquid of the distillate after the distillation (the main distillate and the early distillate) and the residual liquid after the distillation (a post-distillation mixed liquid) was 99.992 area %, and the amount of decomposition was 0.004%, extremely small.

Example 15

A 1-L four-necked flask equipped with a Dimroth condenser, a distillate receiver, a stirrer, and a thermometer necessary for simple distillation operation was charged with 400 g of dimethyl sulfoxide (purity: 99.996 area %) (pure dimethyl sulfoxide: 399.98 g). Next, as an additive, there was charged a sodium carbonate aqueous solution prepared by dissolving 0.4 g of sodium carbonate (0.1 g with respect to 100 g of the pure dimethyl sulfoxide) in 400 g of ion-exchanged water. After substituting the inside of the flask with nitrogen, a rubber balloon filled with nitrogen was mounted at the top of the Dimroth condenser to seal the flask. Under atmospheric pressure, the flask was heated in an oil bath maintained at 220° C., and a point in time when distillation started was considered to be a startup time. An amount of 500 ml containing water as an early distillate was collected. Next, as a main distillation operation, the temperature of the oil bath was decreased to 170° C., and under a pressure of from 150 to 170 Torr, distillate was collected until the amount of a residual liquid in the flask reached 22 g (the amount of water in the residual liquid: 0.0 g) and the amount of the sodium carbonate after the distillation reached 1.9 g with respect to 100 g of the pure dimethyl sulfoxide. Heating time from the startup was 3 hours.

Dimethyl sulfoxide purity in the main distillate was 99.997 area % as shown in Table 4 so that high purity dimethyl sulfoxide was obtained.

Dimethyl sulfoxide purity in the residual liquid was 99.938 area % as shown in Table 4. Dimethyl sulfoxide was hardly decomposed even when heated for 3 hours at 108 to 193° C. (temperatures in the flask) in the early distillation operation and at 138 to 140° C. (temperatures in the flask) in the main distillation operation. Since the amount of the sodium carbonate in the residual liquid was 1.9 g with respect to 100 g of the pure dimethyl sulfoxide in the residual liquid, the sodium carbonate was concentrated to 19 times by distillation of dimethyl sulfoxide.

As shown in Table 4, dimethyl sulfoxide purity in a mixed liquid of the distillate after the distillation (the main distillate and the early distillate) and the residual liquid after the distillation (a post-distillation mixed liquid) was 99.989 area %, and the amount of decomposition was 0.007%, extremely small.

Comparative Example 8

A 1-L four-necked flask equipped with a Dimroth condenser, a distillate receiver, a stirrer, and a thermometer necessary for simple distillation operation was charged with 201 g of dimethyl sulfoxide (purity: 99.996 area %) (pure dimethyl sulfoxide: 200.99 g), without charging any additive. After substituting the inside of the flask with nitrogen, a rubber balloon filled with nitrogen was mounted at the top of the Dimroth condenser to seal the flask. The flask was heated in an oil bath maintained at 220° C., and a point in time when distillation started was considered to be a startup time. When distillate was collected until the amount of a residual liquid in the flask reached 50 g (the amount of water in the residual liquid: 0.0 g), dimethyl sulfoxide purity in the main distillate was 99.972 area % as shown in Table 4. Due to the reduction of the dimethyl sulfoxide purity, the distillation was stopped. Heating time from the startup was 2 hours. Dimethyl sulfoxide purity in the residual liquid was 99.986 area % as shown in Table 4. As shown in Table 4, dimethyl sulfoxide purity in a mixed liquid of the distillate after the distillation (the main distillate) and the residual liquid after the distillation (a post-distillation mixed liquid) was 99.975 area %, and the amount of decomposition was 0.021% that was larger than Example 11.

TABLE 4

| | | Charged liquid | | | Main distillate | | | Residual liquid | | | Purity in post-distillation mixed liquid (area %) | Amount of decomposition (area %) |
| --- | --- | --- | --- | --- | --- | --- | --- | --- | --- | --- | --- | --- |
| | Additive | Dimethyl sulfoxide purity (area %) | Amount of additive (g) | Amount of water (g) | Pressure | Temperatures in flask (° C.) | Dimethyl sulfoxide purity (area %) | Dimethyl sulfoxide purity (area %) | Amount of additive (g) | Additive concentration rate | | |
| Ex 11 | Sodium carbonate | 99.995 | 1 | 0 | Atmospheric pressure | 192-193 | 99.990 | 99.930 | 15 | 15 | 99.986 | 0.009 |
| Ex 12 | Sodium carbonate | 99.995 | 0.86 | 0.14 | Atmospheric pressure | 192-193 | 99.990 | 99.936 | 11.4 | 13 | 99.986 | 0.009 |
| Ex 13 | Sodium carbonate | 99.995 | 0.37 | 0.63 | Atmospheric pressure | 191-193 | 99.990 | 99.951 | 3.4 | 9 | 99.986 | 0.009 |
| Ex 14 | Sodium carbonate | 99.996 | 1 | 5.3 | Atmospheric pressure | 192-193 | 99.995 | 99.956 | 15 | 15 | 99.992 | 0.004 |
| Ex 15 | Sodium carbonate | 99.996 | 0.1 | 100 | Reduced pressure | 138-140 | 99.997 | 99.938 | 1.9 | 19 | 99.989 | 0.007 |
| Com Ex 8 | None | 99.996 | — | 0 | Atmospheric pressure | 192-193 | 99.972 | 99.986 | — | — | 99.975 | 0.021 |

Amount of additive is the amount of an additive with respect to 100 g of the pure dimethyl sulfoxide in the liquid.
Amount of water in charged liquid is the amount of water with respect to 100 g of the pure dimethyl sulfoxide in the liquid.

In Examples 11 to 15, high purity dimethyl sulfoxide was obtained as the main distillates. The dimethyl sulfoxide purity obtained in Comparative Example 8 was lower than Example 11.

The above results showed that our method of purifying dimethyl sulfoxide provided the high purity dimethyl sulfoxide as the main distillates.

Additionally, as purification proceeded by distilling the dimethyl sulfoxide-containing liquid, the decomposition inhibitor remained at a bottom of the distillation column during the purification, thereby increasing concentration of the decomposition inhibitor included in the residual liquid during distillation. In the use of sodium carbonate as the decomposition inhibitor, even when dimethyl sulfoxide was distilled out and the sodium carbonate concentration increased, decomposition of dimethyl sulfoxide was not promoted, and dimethyl sulfoxide purity was high. On the other hand, in the use of sodium hydroxide or potassium carbonate as the decomposition inhibitor, even when added at low concentration, decomposition of dimethyl sulfoxide was promoted when dimethyl sulfoxide was distilled out and the decomposition inhibitor concentration increased. Then, a decomposition product of the dimethyl sulfoxide was contaminated into the distilled dimethyl sulfoxide, thereby reducing dimethyl sulfoxide purity.

INDUSTRIAL APPLICABILITY

Dimethyl sulfoxide obtained by our method of purifying dimethyl sulfoxide has high purity and can be used as solvents in steps of polymerizing and spinning polymers such as polyacrylonitrile, cellulose, polyimide, polysulfone, and polyurethane, stripping liquids for photoresists that are electronic materials, solvents for synthesizing pharmaceuticals and agrochemicals, removing and cleaning liquids for lens molds and the like, or paint stripping liquids.

The invention claimed is:

1. A method of purifying dimethyl sulfoxide comprising distilling a dimethyl sulfoxide-containing liquid in the presence of sodium carbonate in an inert gas atmosphere at atmospheric pressure to distill out dimethyl sulfoxide, an amount of the sodium carbonate with respect to 100 g of pure dimethyl sulfoxide in a residual liquid after the distillation being 6 times or more the amount of the sodium carbonate with respect to 100 g of the pure dimethyl sulfoxide in the dimethyl sulfoxide-containing liquid before the distillation.

2. The method according to claim 1, wherein the distillation is performed by adding, at a start of the distillation, the sodium carbonate in an amount of 0.0005 to 1.0 g with respect to 100 g of the pure dimethyl sulfoxide in the dimethyl sulfoxide-containing liquid.

3. The method according to claim 1, wherein the amount of the sodium carbonate with respect to 100 g of the pure dimethyl sulfoxide in the residual liquid after the distillation is 6 to 1000 times the amount of the sodium carbonate with respect to 100 g of the pure dimethyl sulfoxide in the dimethyl sulfoxide-containing liquid before the distillation.

4. The method according to claim 1, wherein the amount of the sodium carbonate in the residual liquid after the distillation is 0.01 to 100 g with respect to 100 g of the pure dimethyl sulfoxide in the residual liquid after the distillation.

5. The method according to claim 1, wherein, after water in the dimethyl sulfoxide-containing liquid is distilled out as an early distillate, the dimethyl sulfoxide is distilled out as a main distillate.

6. The method according to claim 1, wherein the purified dimethyl sulfoxide has a purity of 99.990 area % or more.

7. The method according to claim 1, wherein the sodium carbonate is used as an inhibitor for dimethyl sulfoxide decomposition.

8. The method according to claim 2, wherein, after water in the dimethyl sulfoxide-containing liquid is distilled out as an early distillate, the dimethyl sulfoxide is distilled out as a main distillate.

9. The method according to claim 3, wherein, after water in the dimethyl sulfoxide-containing liquid is distilled out as an early distillate, the dimethyl sulfoxide is distilled out as a main distillate.

10. The method according to claim 4, wherein, after water in the dimethyl sulfoxide-containing liquid is distilled out as an early distillate, the dimethyl sulfoxide is distilled out as a main distillate.

11. The method according to claim 2, wherein the purified dimethyl sulfoxide has a purity of 99.990 area % or more.

12. The method according to claim 3, wherein the purified dimethyl sulfoxide has a purity of 99.990 area % or more.

13. The method according to claim 4, wherein the purified dimethyl sulfoxide has a purity of 99.990 area % or more.

14. The method according to claim 5, wherein the purified dimethyl sulfoxide has a purity of 99.990 area % or more.

15. The method according to claim 2, wherein the sodium carbonate is used as an inhibitor for dimethyl sulfoxide decomposition.

16. The method according to claim 3, wherein the sodium carbonate is used as an inhibitor for dimethyl sulfoxide decomposition.

17. The method according to claim 4, wherein the sodium carbonate is used as an inhibitor for dimethyl sulfoxide decomposition.

18. The method according to claim 5, wherein the sodium carbonate is used as an inhibitor for dimethyl sulfoxide decomposition.

19. The method according to claim 6, wherein the sodium carbonate is used as an inhibitor for dimethyl sulfoxide decomposition.

* * * * *